United States Patent
Lee et al.

(10) Patent No.: US 10,859,545 B2
(45) Date of Patent: Dec. 8, 2020

(54) SIMPLE EQUILIBRIUM DISTRIBUTION SAMPLING DEVICE FOR GC-MS CALIBRATION

(75) Inventors: Milton L. Lee, Pleasant Grove, UT (US); Xiaofeng Xie, Provo, UT (US); Jacolin A. Murray, Germantown, MD (US); Jesse A. Contreras, Bartlesville, OK (US); Tai Van Truong, Provo, UT (US); H. Dennis Tolley, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 452 days.

(21) Appl. No.: 13/418,016

(22) Filed: Mar. 12, 2012

(65) Prior Publication Data

US 2012/0227461 A1    Sep. 13, 2012

Related U.S. Application Data

(60) Provisional application No. 61/452,033, filed on Mar. 11, 2011.

(51) Int. Cl.
*G01N 30/86* (2006.01)
*G01N 1/28* (2006.01)
(Continued)

(52) U.S. Cl.
CPC ..... *G01N 30/8665* (2013.01); *G01N 30/7206* (2013.01); *G01N 33/0006* (2013.01);
(Continued)

(58) Field of Classification Search
CPC .............. B01L 3/5027; G01N 33/0006; G01N 2001/2893; G01N 2030/047; G01N 30/7206; G01N 30/8665
(Continued)

(56) References Cited

U.S. PATENT DOCUMENTS

| 4,388,272 | A | 6/1983 | Gesteland |
| 5,325,853 | A * | 7/1994 | Morris et al. ............ 204/403.02 |

(Continued)

FOREIGN PATENT DOCUMENTS

| WO | 199714947 A2 | 4/1997 |
| WO | 2007042763 A2 | 4/2007 |

OTHER PUBLICATIONS

Arthur, Catherine L. and Pawliszyn, Janusz. "Solid Phase Microextraction with Thermal Desorption Using Fused Silica Optical Fibers." Anal. Chem. 1990, 62, p. 2145-2148.
(Continued)

*Primary Examiner* — Nimeshkumar D Patel
*Assistant Examiner* — Nashmiya S Fayyaz
(74) *Attorney, Agent, or Firm* — Morriss O'Bryant Compagni Cannon, PLLC

(57) ABSTRACT

A system for providing standard mixtures of volatile and semi-volatile organic compounds for simultaneous GC and MS calibration in a calibration vial, wherein calibration mixtures are prepared by diluting calibration analytes in granular PDMS such that most of the analytes are in the PDMS phase and the sample can then be taken from the analytes in the headspace vapor in the calibration vial, wherein a reliable calibration sample can be taken from the calibration vial because the analytes in the PDMS phase and the headspace vapor are in thermodynamic equilibrium, and wherein the method provides solvent-less sampling, long-time stability, ease of use, is quantifiable, and related to temperature.

17 Claims, 3 Drawing Sheets

(51) Int. Cl.
G01N 30/04 (2006.01)
G01N 30/72 (2006.01)
G01N 33/00 (2006.01)

(52) U.S. Cl.
CPC ............ *G01N 2001/2893* (2013.01); *G01N 2030/047* (2013.01)

(58) Field of Classification Search
USPC .................................................. 73/1.03, 1.06
See application file for complete search history.

(56) References Cited

U.S. PATENT DOCUMENTS

| | | |
|---|---|---|
| 7,258,132 B2 | 8/2007 | Henderson et al. |
| 7,399,449 B1 * | 7/2008 | Oborny et al. .............. 422/504 |
| 2001/0032521 A1 * | 10/2001 | Pawliszyn ............ G01N 1/2214 73/864.71 |
| 2002/0100893 A1 | 8/2002 | Schultz |
| 2003/0015266 A1 | 1/2003 | Wheatley et al. |
| 2009/0044605 A1 | 2/2009 | Shor et al. |

OTHER PUBLICATIONS

Wang, Yanxiang, O'Reilly, John, Chen, Yong, and Pawliszyn, Janusz. "Equilibrium in-fibre standardisation technique for solid-phase microextraction." Journal of Chromatography A., 1072 (2005), p. 13-17.

Namiesnik J et al: "Application of solid-phase microextraction for determination of organic vapours in gaseous matrices" Journal of Chromatography, Elsevier Science Publishers B.V, NL, vol. 885, No. 1-2, Jul. 1, 2000, pp. 405-418.

* cited by examiner

SIMPLE EQUILIBRIUM DISTRIBUTION SAMPLING DEVICE FOR GC-MS CALIBRATION

CROSS REFERENCE TO RELATED APPLICATIONS

This invention document claims priority to and incorporates by reference all, of the subject matter included in the U.S. provisional patent application having Ser. No. 61/452,033 and filed on Mar. 11, 2011.

BACKGROUND OF THE INVENTION

Field of the Invention

This invention relates generally to providing a system for simple, quantitative, portable and reproducible calibration of a gas chromatography-mass spectrometer (GC-MS) system, wherein calibration of the GC is done simultaneously with the MS by using a calibration sample suitable for both devices.

Description of Related Art

Since its inception in the 1950s, gas chromatography-mass spectrometry (GC-MS) has become the most popular and efficient tool to characterize volatile organic mixtures. It is considered to be a mature technique, with widespread availability of a number of commercial GC-MS systems. However, in order to obtain reliable results when using GC-MS, an appropriate calibration procedure must usually be performed before an actual measurement is taken. Compared with the development of GC-ME instrumentation, calibration methods have not changed significantly over the decades; conventional calibration procedures for GC-MS address GC and MS calibration in separate procedures.

The MS is typically calibrated using FC-43 (perfluoro-tributylamine) or other perfluoro-compounds to adjust the MS calibration scale, as well as the relative intensities of MS peaks from low to high mass. By contrast, GC is typically calibrated using liquid or gaseous standard mixtures. It is convenient to use normal alkanes as mixture components to calculate retention indices as well as validate the performance of the capillary column, such as chromatographic efficiency. Other mixtures containing compounds with differing acidity/basicity or polarity can be used to evaluate the inertness of the column and/or the polarity of the stationary phase.

An example of a calibration procedure for GC is for a Liquid standard mixture to be injected into the GC with a syringe. For MS, a calibration procedure might involve introducing FC-43 vapor into the MS from an external calibration vial through a valve.

An important aspect of the present invention is to not only obtain an accurate and reliable calibration of the GC-MS, but to make sure that the process is repeatable many times using the same calibration sample. In the prior art, standard gas mixtures are prepared in large pressurized gas cylinders to ensure constant concentration and multi runs. However, while this method is accurate and repeatable, these gaseous standards are expensive, hard to handle and especially inappropriate for on-site and fast calibration of portable instruments.

Accordingly, conventional GC-MS calibration methods result in several shortcomings. First, the calibration processes are separate for GC and MS. The separate calibration processes increase the time needed for calibration, and this is critical for time-limited applications such as on-site analysis.

In addition, liquid injection of standard solutions is not always good for the instrument (i.e., delay in turning on the ionization source, and sample split are often needed). In additional, long-term stability is a problem for calibration solutions used on a daily basis that contain volatile compounds. Although other alternative calibration methods have been reported, such as precise droplet injection, standard gas mixtures, etc., they are either too complex to perform or can only be applied for limited runs in limited concentration ranges.

Other problems also exist when using a liquid solution for calibration. For example, the liquid can leak out of the container, the liquid is sloshing around in the container when out in the field; compounds in solution also deteriorate after being in solution for a short amount of time. Liquids can also react, they can be adsorbed on the container walls or lid, etc., there are limited numbers of analyses that can be performed, and so there is a limited lifetime for a liquid solution.

A gas sample also has its own unique problems. For example, it is inconvenient to transport a gas tank in the field.

To address sampling and injection of samples in liquid matrices, the technique of solid phase micro extraction (SPME) was introduced in the 1990s and has become a popular and widely used equilibrium based solvent-less sampling method for GC and GC-MS.

In the method of SPME, an adsorbent such as poly (dimethylsiloxane) (PDMS) is coated on a fiber for use in sampling. More generally, due to its inertness and predictable advantages, PDMS has served as an extracting polymer for numerous other equilibrium based techniques. For example, thin PDMS films have been coated inside GC columns; thick PDMS films have been coated on stir bars for sorptive extraction (SBSE) and in capillary tubes for open tubular trapping (OTT); and PDMS particles have been used in extraction cartridges for sampling.

It would be an advantage over the prior art to provide a simple calibration device for validation of both the GC and MS components of a GC-MS system. It would be a further advantage to enable simultaneous calibration of the GC and MS to ensure rapid readiness of the system in the field. This calibration method should be simple, quantitative, reproducible, environmentally-friendly, and robust.

BRIEF SUMMARY OF THE INVENTION

It is an object of the present invention to provide a system for providing standard mixtures of volatile and semi-volatile organic compounds for simultaneous GC and MS calibration in a calibration vial, wherein calibration mixtures are prepared by diluting calibration analytes in granular PDMS such that most of the analytes are in the PDMS phase and the sample can then be taken from the analytes in the headspace vapor in the calibration vial, wherein a reliable calibration sample can be taken from the calibration vial because the analytes in the PDMS phase and the headspace vapor are in thermodynamic equilibrium, and wherein the method provides solvent-less sampling, long-time stability, ease of use, is quantifiable, and related to temperature.

These and other objects, features, advantages and alternative aspects of the present invention will become apparent

DETAILED DESCRIPTION OF THE INVENTION

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

The present invention provides a simple approach for preparing standard mixtures of volatile and semi-volatile organic compounds for simultaneous GC and MS calibration. Instead of dilution with a gas or liquid, the first embodiment of the present invention uses standard vapor mixtures using PDMS particles to dilute thirteen calibration compounds, which also serve as a can rant reservoir.

In a closed container, standard mixture components partition between poly(dimethylsiloxane) (PDMS) particles and headspace to provide constant vapor concentrations. The granular form of heat-conditioned PDMS serves as a standard reservoir or calibrant reservoir, which provides fast equilibrium with the headspace vapor. Both the GC and MS components of the instrument can be calibrated with vapors generated with this device. Quantitative calibration can be achieved with either active temperature control or by using a previously constructed look-up table.

Constant headspace vapor concentration is achieved by rapid partition of analytes between granular heat-conditioned PDMS and headspace. Rapid partitioning or increasing the rate of partitioning is made possible because of the large surface area of the PDMS that allows for rapid transition of the analytes to a vapor. The analytes are sampled from the headspace by SPME, for example, and transferred to the GC-MS for calibration analysis. Once there is thermodynamic equilibrium distribution between the headspace vapor and the liquid analytes absorbed by the PDSM, the standard vapor sample or calibration sample in the calibration sample vial can be used. If a known amount of liquid analytes is placed in the calibration sample vial and is absorbed by the PDMS, it is possible to calculate how much of the analyte is in the headspace vapor.

Figure 1:
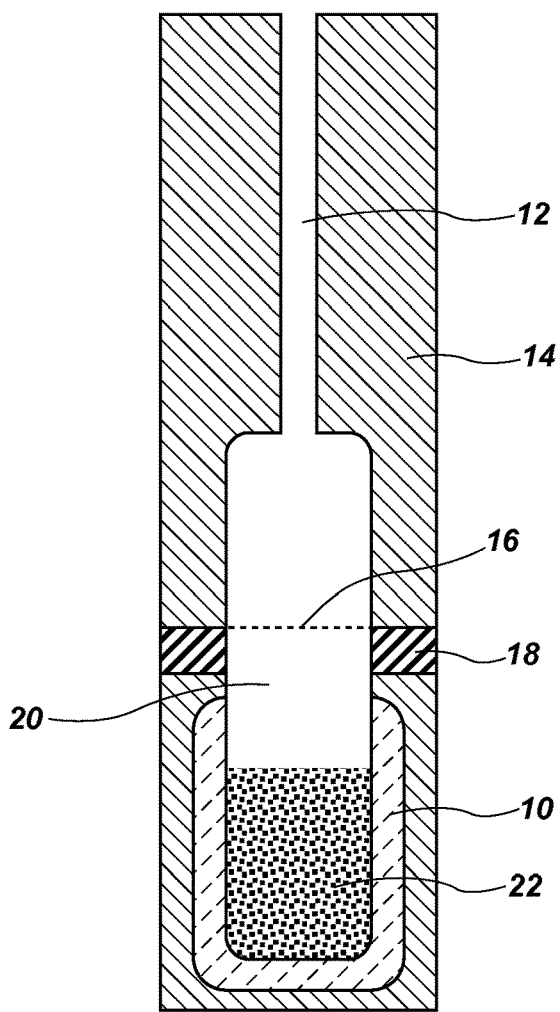
FIG. 1 is provided as a block diagram of the components of the present invention, including a vial showing PDMS particles and the headspace above.

FIG. 1 is provided as a block diagram of the components of the present invention in a first embodiment, FIG. 1 shows a vial 10 having an inlet tube 12, a cap, 14, a screen 16, a seal 18, headspace 20 and PDMS 22.

Figure 2:
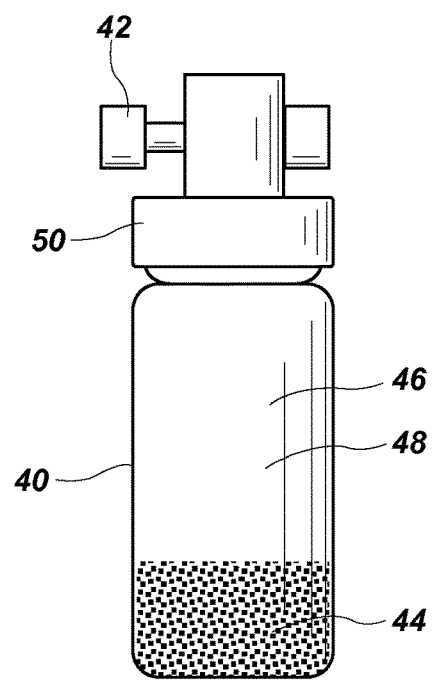
FIG. 2 shows an alternative embodiment of the present invention wherein a screen is not required.

In FIG. 2, an alternative embodiment simplifies the design of FIG. 1. As shown, no screen is needed in the vial. The vial 40 includes a sample port 42 that enables the taking of calibration samples. The vial 40 includes a calibrant reservoir 44, a headspace volume 46 wherein the headspace vapor 48 accumulates, and a cap 48. The calibration samples are taken from the headspace vapor 48.

It is well known that the conventional calibration compound for MS, FC-43, is not applicable to GC. Likewise, typical test compounds for GC, such as the normal alkanes and polarity mixtures, such as the Grob test mixture, are not particularly useful for MS calibration. Therefore, in order to calibrate the GC and MS with one test sample, a calibration mixture is needed that contains: (a) normal alkanes to index compound retention with the Kovats retention indices, RI, and to indicate chromatographic efficiency, (b) compounds with a variety of polarities to test for GC column inertness and polarity, and (c) compounds that produce mass fragments that cover the mass range of interest in MS. Perfluorotributylamine (FC-43) has characteristic mass fragments (m/z) from electron ionization (EI) of 69, 100, 119, 131, 219, 262, 414, and 464.16.

To fulfill the requirements for MS, the following compounds were selected which provide the m/z values in parenthesis: methyl-tert-butyl (73), methylcyclohexane (55, 83), Toluene d-8 (98, 100), tetrachloroethene (94, 129, 166), bromopentafluorobenzene (117, 167, 146, 248), bromoform (1771, 173, 175), 1,2-dibromotetrafluorobenzene (148, 306, 308, 310), methyl salicylate (92, 120, 152), and tetrabromoethane (184, 186, 188, 263, 265, 267, 269, 346). These compounds not only provide peaks that cover m/z values from 55 to 346, but also many characteristic isotopic peaks which helped to calibrate the mass spectrometer.

For GC, dichloromethane (RI=333), heptane (RI=700), pentadecahe (RI=1500) and diethylphthalate (DEP, RI=1603) covered the GE retention range from 333 to 1603. Not all of these test analytes are necessary for all applications; it should be understood that any of these or other compounds can be added to the calibration vial to meet specific calibration needs.

The materials used in preparing the calibration vial used in the first embodiment of the present invention contained the following components and were obtained from the following sources. Dichloromethane (HPLC grade, 99.9%) and n-heptane (97%) were obtained from Mallinckrodt (NJ, USA). Toluene (HPLC, 99.8%), n-octane (99%), n-nonane (99%), 1,1,2-tetrabromoethane (lab grade) and methyl salicylate (99%) from Fisher Scientific (PA, USA), n-decane (99%) Were obtained from Spectrum (NJ, USA). All other chemicals were from Sigma Aldrich (MO, USA), including diethyl phthalate (99.5%), n-dodecane (99%), tetrachloroethene (99%), 1,2-dibromotetrafluorobenzene (97%), methyl-tert-butyl ether (99.8%), toluene d-8 (99.6%), methylcyclohexane (99%), bromoform (99%), bromopentafluorobenzene (99%), butylbenzene (99%), n-undecane (99%) and n-pentadecane (99%). Sylgard® 184 silicone elastomer kit was obtained from Dow Chemical (MI, USA).

Regarding the instrumentation used in performing tests, all tests were conducted using an Agilent 5890 GC system coupled with an Agilent 5972 MS detector and an Agilent GC 7820A with FID detector. The operating conditions included full scan mode (MS detector), temperature program with initial temperature of 40° C. for 0.5 min, and then ramp to 200° C. at 30° C./min, with a final hold for 0.23 min (total run time of 6.13 min.).

An important aspect of the present invention is the preparation of the granular PDMS particles that are placed in the calibration vial. Sylgard® 184 silicone elastomer and initiator were mixed together according to the instructions that came with the kit at a ratio of 10:1, and then vacuum, was applied at 27 in. Hg for 2 hours for degassing. The mixture was polymerized at 100° C. for 35 min, followed by cutting the PDMS into small blocks (approximately 3 mm square). The chopped PDMS blocks were then baked at 250° C. for 8 hours to remove the last traces of solvent, and finally ground into granular form with a glass rod and sieved between 1 mm and 180 μm sieves.

During testing of the PDMS material, a solid. PDMS plug was used initially in the calibration vial. However, it was discovered that it took a long time for the analytes in the PDMS to reach equilibrium with the headspace vapor. However, by grinding the PDMS material into small particles, the larger surface area of the PDMS granules enables equilibrium to be reached substantially faster.

Another aspect of the invention is the type of materials that can be used to hold the analytes. It is believed that the analytes can adhere to a solid using the processes of absorption as with PDMS or through adsorption. Adsorption might be possible using carbonaceous materials, other polymeric materials, silica, Tenax, or materials containing similar properties that will enable absorption or adsorption of analytes. Thus a calibrant reservoir for the diluted analytes is prepared through either absorption or adsorption on to a suitable material.

For testing purposes of the present invention, glass 2-dram vials were capped with Mininert® valves. A designated amount of granular PDMS (1-2 g) was introduced into each calibration vial, and pure liquid analytes were dispersed on the PDMS. The initial equilibrium distribution required from 2 hours to 2 days depending on the volatilities of the analytes.

A distinct advantage of the present invention is that once the calibration vial has been prepared, it is capable of being stored for long periods of time, but for at least 12 months or longer. It would be a significant improvement over the prior art to state that calibration samples can be taken 6 months apart without a substantial change in concentration in the headspace vapor. In addition, hundreds of calibration samples can be taken from the calibration vial with very little change in concentration as will be explained. Once equilibrium is reached, the headspace vapor can be sampled. For example, an SPME fiber containing 100 μm film of PDMS was used to deliver the analytes from the vial to a GC injection port, where sampling was done for 30 seconds.

Figure 3:
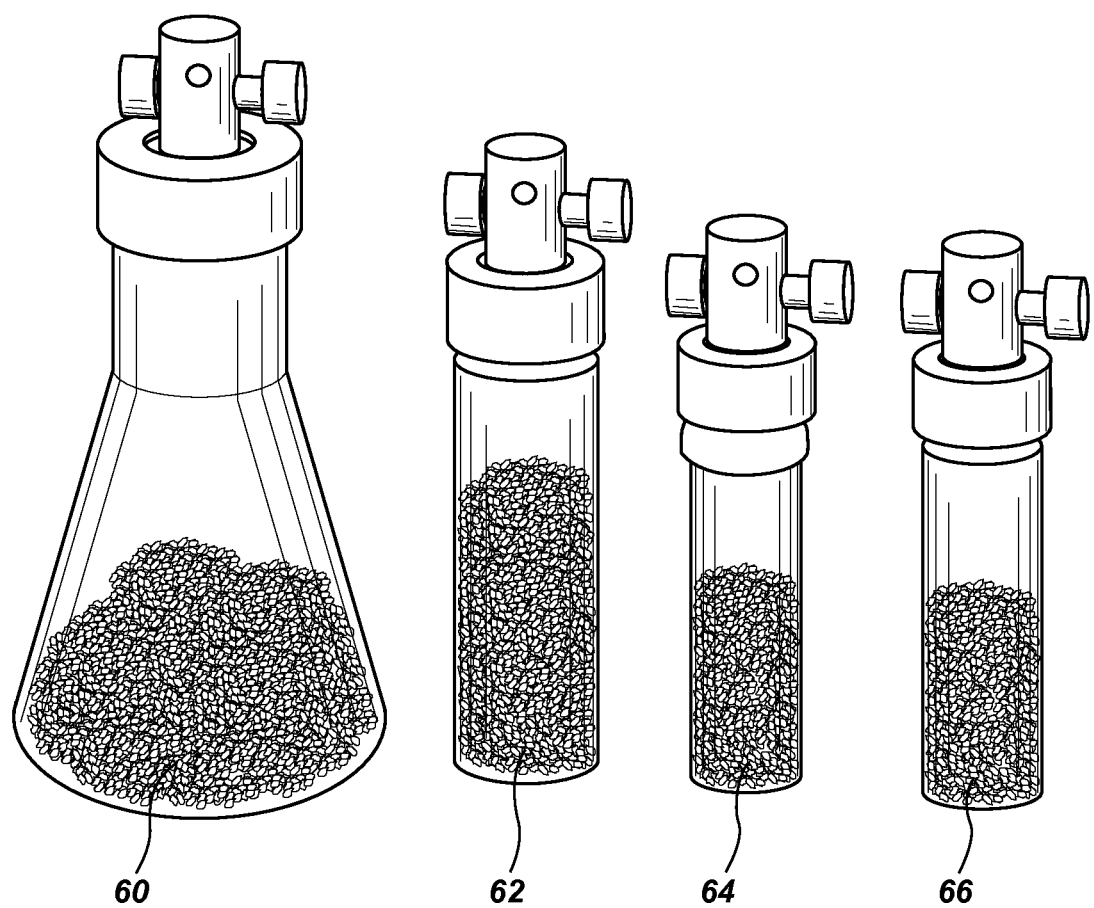
FIG. 3 is a line drawing showing a plurality of calibration vials having different types of PDMS particles and headspace volumes.

FIG. 3 is a line drawing of several calibration vials of different sizes and containing different PDMS particle sizes. From left to right: 50-mL vial 60 with small PDMS chunks, 4-dram vial 62 with PDMS chunks, 2-dram vial 64 with PDMS chunks, and a 2-dram vial 66 with PDMS particles.

Long term use and stability of the sample in the calibration vial are important characteristics of a calibration sample system, and the performance of the present invention was evaluated.

Figure 4:
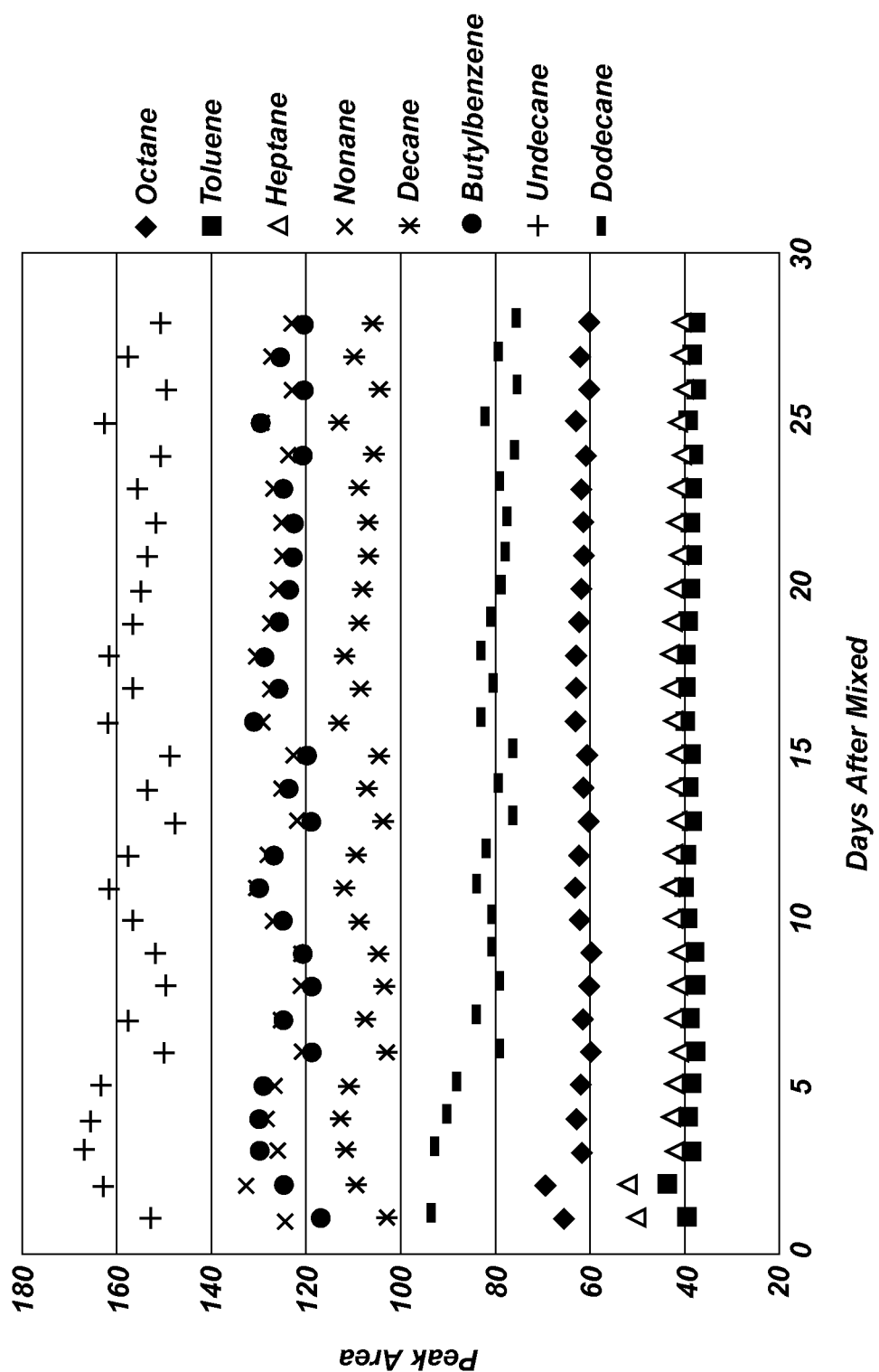
FIG. 4 is a graph of GC relative peak area versus time for a 2-dram calibration vial containing 3.0 grams of granular PDMS and eight test analytes.

FIG. 4 is a graph of GC relative peak area versus time for a 2-dram calibration vial containing 3.0 grams of granular PDMS and eight test analytes. Specific amounts of toluene, n-heptane, n-nonane, n-decane, butylbenzene, n-undecane, and n-dodecane were introduced into the 2-dram vial. An SPME fiber (100 μm thick PDMS) was used to sample the headspace (room temperature, 21-23° C., 30 seconds sample time, static sampling without agitation) for approximately three times a day. After 28 days and more than 100 samplings, no significant signal decrease was observed; the fluctuation in signal was a result of temperature variations in the room. The variation between different devices was less than 8%.

The partition coefficients of the analytes between headspace and PDMS phase determine the concentrations or amounts in the two phases at equilibrium. From the basic distribution theory, we can calculate the partition coefficients by preparing vials with different PDMS amounts and headspace volumes.

For large K, it was determined that the PDMS serves as a good test analyte reservoir; i.e., the major fraction of each analyte was in the PDMS phase. The large partition coefficients also confirmed observations that a large number of runs can be made before any significant reduction in signal is noticed (i.e., since most of the analyte is in the PDMS phase, each sampling from the headspace depletes only a very small fraction of the total amount of the analyte in the calibration vial).

Another important characteristic for the calibration device is the time required for establishment of distribution equilibrium between samplings, i.e., how long it takes for the device to be ready for use between the extraction of calibration samples. The equilibrium time was measured from room temperature (approximately 23° C.) to 40° C. For a beginning at equilibrium from the lower temperature, it took 10 minutes to re-establish equilibrium at the higher temperature (peak area >98% of the equilibrium condition peak area). For a re-equilibrium time of 10 minutes, the RSDs between different tests were below 4.5%. The least volatile compound tested was n-dodecane. This demonstrates that the partitioning of analytes between the PDMS and headspace is relatively last. Therefore, it is possible that analytes in the PDMS can rapidly move from the PDMS into the headspace to re-establish the headspace vapor concentration for subsequent calibrations.

In order to perform quantitative calibration, either an active temperature control device or a previously generated look-up table is needed to give the true amount sampled as a function of temperature. A look-up table for a temperature range of 4° C. to 50° C. for eleven compounds is given in Table 1. The true amounts can be provided for other compounds as well, and this list should only be considered as a sample of what can be provided. The peak areas for all except the most volatile compounds were linearly related to temperature. Using this table, the peak area can be calculated for any given temperature within the range studied.

TABLE 1

Look-up table based on 11 standard compounds (1-11), at temeratures of 4° C., 25° C., 30° C., 35° C., 40° C., and 50° C.(data are listed as relative peak areas).

|  | 1 | 2 | 3 | 4 | 5 | 6 | 7 | 8 | 9 | 10 | 11 |
|---|---|---|---|---|---|---|---|---|---|---|---|
| 4° C. | 216.25 | 129.78 | 32.81 | 73.84 | 87.06 | 92.78 | 113.91 | 47.61 | 26.04 | 40.04 | 4.71 |
| 25° C. | 235.05 | 179.01 | 44.11 | 87.76 | 115.91 | 140.64 | 153.33 | 123.32 | 85.97 | 125.32 | 26.50 |

TABLE 1-continued

Look-up table based on 11 standard compounds (1-11), at temeratures of 4° C., 25° C., 30° C., 35° C., 40° C., and 50° C.(data are listed as relative peak areas).

| | 1 | 2 | 3 | 4 | 5 | 6 | 7 | 8 | 9 | 10 | 11 |
|---|---|---|---|---|---|---|---|---|---|---|---|
| 30° C. | 240.07 | 197.75 | 47.91 | 94.49 | 126.50 | 156.94 | 169.48 | 158.13 | 117.93 | 168.37 | 41.97 |
| 35° C. | 233.13 | 203.89 | 48.77 | 96.12 | 130.74 | 168.31 | 178.62 | 191.92 | 149.70 | 215.61 | 56.91 |
| 40° C. | 231.25 | 210.28 | 50.36 | 98.06 | 135.43 | 179.43 | 187.53 | 225.33 | 183.46 | 262.01 | 77.25 |
| 50° C. | 239.70 | 236.40 | 55.44 | 105.74 | 146.80 | 200.98 | 207.77 | 303.76 | 281.05 | 387.61 | 150.67 |
| $R^2$ with 4° C. value | 0.63 | 0.99 | 0.99 | 0.99 | 0.99 | 1.00 | 1.00 | 0.96 | 0.91 | 0.92 | 0.80 |
| $R^2$ without 4° C. value | 0.02 | 0.97 | 0.97 | 0.96 | 0.98 | 0.99 | 0.99 | 1.00 | 0.99 | 0.99 | 0.95 |

It is noted that Compounds 1-11 are methylene chloride, methyl-tert-butyl ether, methylcyclohexae, toluene-d8, perchloroethylene, bromopentafluorobenzene, bromofrom, dibromotetrafluorobenzene, methyisalicylate, tetrabromoethane, and n-pentadecane. It is also noted that R-squared values ($R^2$) were calculated with and without 4° C. data.

This simple approach can be used in other applications, such as construction of calibration curves, sampling with tubes containing granular PDMS particles followed by headspace sampling for analysis, and standard gas preparation. One of the most useful implementations is on-site or real-time construction of calibration curves for GC-MS instrumentation.

Calculation of the partition coefficients is possible using the following equations. First we begin with the two equations (1) $M=X1Vg1+Y1Vs1$ and (2) $M=X2Vg2+Y2Vs$ where X1, X2, Y1, and Y2 represent solute concentrations in the headspace and solid phase of the vial with volumes of Vg1, Vg2, Vs1, and Vs2, respectively. M is the total amount of solute in the vial. By combining Equations 1 and 2 we obtain the equation (3) $X1V1+Y1Vs1=X2V2+Y2Vs2$. If the distribution equilibrium constant, K, is defined as follows (4) $Y2=K\,X2$, and (5) $Y1=K\,X1$, then Equation 3 becomes (6) $X1Vg1+KX1Vs1=X2Vg2+KX2Vs2$, and (7) $X1(Vg1+KVs1)=X2(Vg2+KVs2)$, which becomes (8) $X2/X1=(Vg1+KVs1)/(Vg2+KVs2)$. If A is then defined to be (9) $A=X2/X1=$ Peak Area 2/Peak Area 1, then K can be determined from experimental results according to (10) $K=(AVg2-Vg1)/(Vs1-AVs2)$. If K is known accurately, the concentration change in the headspace with respect to any change in headspace and solid phase volumes can be calculated using Equation 10. X2/X1 is the correction factor for any change in volumes of the two phases. K is experimentally determined, and depends on sample conditions, sample matrices (number of components and partial pressures of the solutes). K is independent of N.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements. It is also understood that the described invention can be applied to GC or MS alone, without each other, and to other chemical analysis instrumentation that requires calibration or testing using a gaseous standard.

The invention claimed is:

1. A method for creating a standard vapor sample from a non-liquid sample source in a closed container, said method comprising the steps of:

providing non-liquid calibration analytes in a calibrant reservoir;

disposing the calibrant reservoir in a sample vial where no liquid is present such that there is a headspace volume above the calibrant reservoir;

diluting the non-liquid calibration analytes in the calibrant reservoir and allowing a thermodynamic equilibrium to be established between the headspace vapor and the calibration analytes before the calibration sample is extracted from the sample vial;

providing a granular form of heat-conditioned polydimethylsiloxane (PDMS) to function as the calibrant reservoir for the diluted calibration analytes;

allowing thermodynamic equilibrium to be established between the non-liquid calibration analytes in the calibrant reservoir and headspace vapor in the sample vial, wherein the sample vial is closed to create the thermodynamic equilibrium;

extracting a calibration sample from the headspace vapor using solid phase microextraction (SPME), wherein the calibration sample is suitable for gas chromatograph (GC) and mass spectrometer (MS) calibration.

2. The method as defined in claim 1 wherein the method further comprises the step of calibrating a device using the calibration sample from the headspace volume.

3. The method as defined in claim 2 wherein the method further comprises the step of selecting the device to be calibrated from the group of devices comprised of: a gas chromatography-mass spectrometer (GC-MS) system, a mass spectrometer system, and a gas chromatograph system.

4. The method as defined in claim 1 wherein the method further comprises the step of providing an adsorbent material as the calibration reservoir.

5. The method as defined in claim 1 wherein the method further comprises the step of performing solvent-less sampling.

6. The method as defined in claim 1 wherein the method further comprises the step of performing quantitative calibration as a function of temperature.

7. The method as defined in claim 6 wherein the method further comprises the step of performing the quantitative calibration using active temperature control in order to determine an accurate amount sampled as a function of temperature.

8. The method as defined in claim 6 wherein the method further comprises the step of performing the quantitative calibration using a look-up table in order to determine an accurate amount sampled as a function of temperature.

9. The method as defined in claim 1 wherein the method further comprises the step of enabling the non-liquid diluted analytes in the calibrant reservoir to reestablish thermodynamic equilibrium between the calibrant reservoir and the headspace vapor.

10. The method as defined in claim 1 wherein the method further comprises the step of increasing a rate of partitioning of the analytes into headspace vapor by providing a large surface area for the material used as the calibrant reservoir.

11. The method as defined in claim 1 wherein the method further comprises the step of re-establishing equilibrium of the headspace vapor in less time than it takes to establish initial equilibrium.

12. The method as defined in claim 1 wherein the method further comprises the step of extracting a plurality of calibration samples, wherein thermodynamic equilibrium is re-established between taking each calibration sample.

13. The method as defined in claim 1 wherein the method further comprises the step of enabling constant headspace vapor to be established in the headspace volume if there is at least six months between calibration samples.

14. The method as defined in claim 1 wherein the method further comprises the step of real-time construction of calibration curves.

15. The method as defined in claim 1 wherein the method further comprises the step of increasing vapor concentration of the headspace vapor by increasing a temperature of the calibration analytes in the calibration reservoir.

16. A calibration sample system for creating and holding a standard vapor sample from a non-liquid sample source, said system comprised of:
 a sample vial having a cap thereon for sealing contents inside;
 a calibrant reservoir disposed in the sample vial;
 non-liquid calibration analytes that are stored in the calibrant reservoir, wherein the calibrant reservoir is comprised of a granular form of heat-conditioned polydimethylsiloxane (PDMS);
 a headspace volume comprising all space within the sample vial that is not occupied by the calibrant reservoir;
 headspace vapor that fills the headspace volume and is in thermodynamic equilibrium between the non-liquid calibration analytes and the headspace vapor in the sample vial;
 a valve that is opened to enable access to the headspace vapor in the headspace volume and which is closed to create the thermodynamic equilibrium; and
 a solid phase microextraction device (SPME) for extracting a standard vapor sample from the headspace volume.

17. The system as defined in claim 16 wherein the calibrant reservoir is further comprised of an adsorbent material.

\* \* \* \* \*